United States Patent [19]

Golias

[11] 4,105,521

[45] Aug. 8, 1978

[54] CLINICAL PROCEDURE FOR MEASURING LIPOPROTEIN CHOLESTEROLS

[75] Inventor: Tipton Golias, Beaumont, Tex.

[73] Assignee: Helena Laboratories Corporation, Beaumont, Tex.

[21] Appl. No.: 835,387

[22] Filed: Sep. 21, 1977

[51] Int. Cl.$^2$ ............................................. G01N 27/26
[52] U.S. Cl. ........................... 204/180 S; 204/180 G; 204/299 EC
[58] Field of Search ............... 204/180 S, 180 G, 299; 23/230 B

[56] References Cited

U.S. PATENT DOCUMENTS

| | | | |
|---|---|---|---|
| 3,607,695 | 9/1971 | Schneider | 204/180 S |
| 3,759,773 | 9/1973 | Dwyer et al. | 204/180 S X |
| 3,808,118 | 5/1974 | Golias | 204/180 S X |
| 3,873,433 | 3/1975 | Seidel et al. | 204/180 S X |

*Primary Examiner*—Arthur C. Prescott
*Attorney, Agent, or Firm*—Cullen, Settle, Sloman & Cantor

[57] ABSTRACT

An electrophoresis method of determining the concentration of high density lipoprotein (HDL) cholesterol in body fluids and simultaneously determining the concentrations of very low density lipoprotein (VLDL) and low density lipoprotein (LDL) cholesterols in the fluid. The method includes applying a small sample of the fluid to an electrophoresis support medium, applying a direct current across the medium, applying a developing substrate to the electrophoresed lipoproteins and quantitatively determining the concentration of each lipoprotein cholesterol. This method does permit direct and simultaneous measurement of each lipoprotein cholesterol fraction while eliminating precipitation of each fraction as required by the prior art.

12 Claims, No Drawings

CLINICAL PROCEDURE FOR MEASURING LIPOPROTEIN CHOLESTEROLS

FIELD OF THE INVENTION

The present invention relates to a clinical method of determining the concentration of lipoprotein cholesterol fractions, particularly high density lipoprotein (HDL) cholesterol in serum, plasma and other body fluids.

Blood serum cholesterol has been recognized for over thirty years as associated with coronary artery diseases. Medical experts have long believed that persons having elevated serum cholesterol levels are more likely to suffer myocardial infarction (heart attack) than persons having lower levels of cholesterol. However, the correlation between cholesterol levels and coronary artery disease is not consistent and therefore the present diagnostic tests for cholesterol are considered advisory only and not a reliable indicator of the likelihood of myocardial infarction or premature coronary artery disease.

The more recent work by the National Heart, Lung and Blood Institute of Bethesda, Md. and the Framingham Heart Institute of Framingham, Mass. has suggested that one fraction of cholesterol, high density lipoprotein, is actually a "predictor of inverse cardiovascular risk". This discovery should improve our understanding of the role of cholesterol in coronary artery diseases. Further, a correlation between the remaining lipoprotein cholesterol fractions and cardiovascular risk may also be found. Therefore, a simple, fast and reliable test for the concentrations of lipoprotein cholesterol fractions in body fluids is necessary.

The present clinical tests for determining the concentration of high density lipoprotein (HDL) cholesterol in body fluid requires precipitation of the other cholesterol fractions (low density and very low density lipoproteins) and determination of the cholesterol concentration in the supernate. Briefly, the recommended test includes adding heparin solution to the fluid sample and mixing, adding manganese chloride and mixing, chilling and drawing off the supernate. All of the cholesterol remaining in the supernate is assumed to be high density lipoprotein cholesterol. The cholesterol is extracted with isopropanol and the extract assayed for cholesterol and triglyceride in spectro photometers or continuous-flow analyzers.

It will be apparent that this procedure has several disadvantages. The procedure is slow and therefore expensive. Because precipitation is used, the reliability of the test is suspect. Finally, the assumption that all of the cholesterol remaining after precipitation is high density lipoprotein has been seriously questioned. The problem with this assumption is the lack of specificity of the commonly used cations, specifically $Ca^{2+}$, $Mg^{2+}$ and $Mn^{2+}$, in the lipoprotein-heparin interaction. Further, it has been found that subclasses of high density lipoproteins can be precipitated in the presence of manganese cations. Thus, the precipitation method may not be as reliable as believed.

The method of determining the concentration of lipoprotein cholesterol fractions of the present invention eliminates these problems and provides a simple and reliable clinical procedure.

SUMMARY OF THE INVENTION

Cholesterol occurs in blood serum in two forms, namely free cholesterol and cholesterol esters. Both forms are bound to serum proteins along with other lipids (i.e., triglycerides, phospholipids, et cetera) to form lipoproteins. These lipoproteins occur in different densities as initially determined by ultracentrifugation. The density fractions are generally referred to as high density lipoprotein (HDL) cholesterol, very low density lipoprotein (VLDL) cholesterol and low density lipoprotein (LDL) cholesterol. It will be understood that further fractions have been identified including subclasses of HDL cholesterol, however these are the principal fractions.

Although certain proteins have been separated by electrophoresis methods, such methods have not been successful in separating smaller molecules such as cholesterol. The method of this invention takes advantage of the fact that both forms of cholesterol are bound to serum proteins, permitting separation by electrophoresis methods. As described, the method of this invention permits simultaneous determination of the concentrations of high density lipoprotein, very low density lipoprotein and low density lipoprotein cholesterols in body fluids such as serum, plasma, etc. The procedure is as follows.

First, a small sample of the body fluid to be tested is applied to a solid electrophoresis support media, preferably cellulose acetate. The support media will generally be in the form of a strip. Next, a direct current is applied across the support media for a predetermined time to separate the high density, very low density and low density lipoprotein cholesterols on the media. Next, a developing substrate sensitive to small concentrations of cholesterol is applied to the electrophoresed lipoprotein cholesterols, developing the separated lipoprotein cholesterols on the support media, the cholesterols appearing reddish-brown in color. Finally, the concentrations of each of the lipoprotein cholesterols may be quantitatively determined by one or any of several methods, including direct densitometry or by eluting each fraction and measuring the concentration of each lipoprotein in the eluate.

The method of the present invention thus permits simultaneous measurement of high density lipoprotein cholesterol, low density lipoprotein cholesterol and very low density lipoprotein cholesterol. The procedure is faster and less costly than the present clinical methods because the procedure of the present invention eliminates precipitation. Finally, the method of the present invention is more reproducible because the determination of the lipoprotein cholesterol concentrations are made directly from the entire sample. Other advantages and meritorious features of the present invention will be more fully understood from the following detailed description.

DETAILED DESCRIPTION OF THE METHOD OF THIS INVENTION

The method of determining concentrations of lipoprotein cholesterols of this invention is basically an electrophoretic determination. Thus, a small sample of the body fluid to be tested is first applied to a solid electrophoresis support media, preferably cellulose acetate. A suitable cellulose acetate support media is available in strip form from the assignee of the present invention under the trade name "Titan III". It will be understood that other support media including cellulose nitrate, agar, agarose, paper acrylamide gel, cellulose nitrate, silica gel, starch gel, etc. may also be used. The fluid sample is preferably applied to the support media in a straight line, permitting accurate reading following electrophoresis. A suitable apparatus for applying the fluid sample to the support media is disclosed in U.S. Pat. No. 4,006,705.

Next, a direct electric current is applied across the media, causing separation of the lipoprotein cholesterol fractions. Movement of the lipoprotein cholesterols through a medium such as cellulose acetate depends upon the medium, the intensity of the electric field, the time and the character of the charged particle. In view of the fact that these variables will be constant for each lipoprotein cholesterol fraction, the fractions are separated upon application of the electric field. It has been found that optimum separations for lipoprotein cholesterols occur at about 180 volts (DC) for about 20 minutes. It has been found that the order or separation is HDL, VLDL and LDL cholesterol, which is the order given herein.

Following electrophoresis, a developing substrate sensitive to small concentrations of cholesterol is applied to the electrophoresed lipoprotein cholesterol strip. In the preferred embodiment, the developing substrate is a cholesterol oxidase-esterase substrate such as available from Worthington Biochemical Corporation, Freehold, N.J. The cholesterol oxidase-esterase available from Worthington Biochemical Corporation is used to measure enzymatic cholesterol. In the method of the present invention, the electrophoresed lipoprotein cholesterols are incubated with the cholesterol oxidase-esterase substrate for about 15 minutes at 37° C. The developing substrate may be applied to the electrophoresed cholesterols by one of several methods, including simply soaking or submerging the support media in the reagent or, more preferably, sandwiching the support media to another support media that has been impregnated with the reagent. For example, a strip of celulose acetate as described above may be soaked or impregnated with cholesterol oxidase-esterase reagent. A sandwich of a strip of cellulose acetate impregnated with the reagent and the electrophoresed media is then made, which is incubated as described above.

Where the developing substrate is a cholesterol oxidase-esterase reagent, the lipoprotein cholesterols are stained a reddish-brown color and are easily visualized on the support media. Further, as described, the lipoprotein fractions have been separated during electrophoresis, permitting quantitative determination of the concentration of the high density lipoprotein, very low density lipoprotein and low density lipoprotein cholesterols.

Quantitation may be accomplished by one of several methods. In the simplest method, the support media is scanned by a suitable instrument for measuring absorbence, such as a densitometer. Alternatively, the individual fractions may be eluted and the absorbence measured by a spectrophotometer. As will be understood by those skilled in the art, other quantitative methods may also be utilized. For example, the cholesterol oxidase-esterase reagent may be tagged with fluorescene or a radioactive isotope, such as iodine 125. Where fluorescene is used, the concentration of each fraction may be determined by a fluorescent densitometry or spectrophotometry. Where a radioactive isotope is utilized, the concentrations are determined by measuring the radioactivity of each sample using a radioisotope scanner. Additionally, where a thin sheet or strip of cellulose acetate is used for the electrophoresis support medium, the individual lipoprotein fractions may be cut out with scissors. Then, each fraction may be dissolved and the fluorescence or radioactivity of each sample measured. This provides a very accurate determination.

It will be understood by those skilled in the art that various modifications may be made to the method of determining the concentration of lipoprotein cholesterols of this invention. Further, details of the electrophoretic method will be understood by those skilled in the art. For example, U.S. Pat. No. 4,005,434 discloses a method and apparatus for graphic densitometer display which may be used in the method of this invention.

I claim:

1. A method of simultaneously determining the concentrations of high density lipoprotein cholesterol, very low density lipoprotein cholesterol and low density lipoprotein cholesterol in a sample of body fluid, comprising the steps of:
   (a) applying a small sample of said body fluid to be tested to a solid electrophoresis support media strip,
   (b) applying a direct current for a predetermined period of time to said support media until the high density, very low density and low density lipoprotein cholesterols have separated on the media,
   (c) applying a developing substrate sensitive to small concentrations of cholesterol and cholesterol esters to the electrophoresed lipoprotein cholesterol strip, and
   (d) quantitatively determining the concentrations of high density lipoprotein, very low density lipoprotein and low density lipoprotein cholesterols in said body fluid sample from the developed electrophoresed sample.

2. The method of determining concentrations of lipoprotein cholesterols in a sample of body fluid defined in claim 1, wherein said developing substrate is a cholesterol oxidase-esterase substrate which is applied to said electrophoresis support media.

3. The method of determining concentrations of lipoprotein cholesterols in a sample of body fluid defined in claim 2, wherein said cholesterol oxidase-esterase is applied to said support media by immersing the media in a fluid sample of said cholesterol oxidase-esterase reagent.

4. The method of determining concentrations of lipoprotein cholesterols in a sample of body fluid defined in claim 2, wherein said cholesterol oxidase-esterase substrate is applied to said support media by impregnating an untreated strip of support media with fluid cholesterol oxidase-esterase reagent and applying said impregnated strip to the electrophoresed lipoprotein cholesterols in a sandwich form and incubating the sandwiched media for a predetermined period of time.

5. The method of determining concentrations of lipoprotein cholesterols in a sample of body fluid defined in claim 1, wherein said electrophoresis support media is cellulose acetate and said direct current is about 180 volts which is applied to said support media for about 20 minutes.

6. The method of determining concentrations of lipoprotein cholesterols in a sample of body fluid defined in claim 1, wherein the concentrations of the lipoprotein are quantitatively determined by a densitometer by measuring absorbance of each lipoprotein cholesterol following application of the developing substrate.

7. The method of determining concentrations of lipoprotein cholesterols in a sample of body fluid defined in claim 1, wherein said quantitative determination is made by eluting each electrophoresed fraction, including high density lipoprotein, very low density lipoprotein and low density liproprotein cholesterol and then quantitatively determining the concentration of each fraction.

8. The method of determining concentrations of liproprotein cholesterols in a sample of body fluid defined in claim 7, wherein the concentration of each fraction is determined using a spectrophotometer.

9. The method of determining concentrations of liproprotein cholesterols in a sample of body fluid defined in claim 7, wherein said cholesterol oxidase-esterase reagent is tagged with fluorescene, including quantitatively determining the concentration of each fraction by measuring the fluorescence.

10. The method of determining concentrations of liproprotein cholesterols in a sample of body fluid defined in claim 7, wherein said cholesterol oxidase-esterase is tagged with a radioactive isotope, including quantitatively determining the concentration of each fraction by measuring the radioactivity of each fraction with a radioisotope counter.

11. A method of determining the concentration of high density liproprotein cholesterol in body fluid, comprising:
 (a) applying a small sample of said body fluid to a solid electrophoresis support media,
 (b) applying a direct current across said electrophoresis support media until the high density lipoprotein cholesterol has separated from any remaining liproprotein in said sample,
 (c) applying a developing substrate sensitive to high density liproprotein cholesterols to the separated electrophoresed high density lipoprotein cholesterol, and
 (d) quantitatively determining the concentration of the high density lipoprotein cholesterol present in said body fluid from said developed electrophoresed sample.

12. The method of determining the concentration of high density lipoprotein cholesterol in a fluid sample defined in claim 11, wherein said developing substrate is a cholesterol oxidase-esterase substrate and said support media is cellulose acetate, including applying said cholesterol oxidase-esterase to the electrophoresed sample on said cellulose acetate media.

* * * * *